United States Patent
Babij et al.

(10) Patent No.: US 10,787,431 B2
(45) Date of Patent: Sep. 29, 2020

(54) 4-((6-(2-(2,4-DIFLUOROPHENYL)-1,1-DIFLUORO-2-HYDROXY-3-(5-MERCAPTO-1H-1,2,4-TRIAZOL-1-YL)PROPYL)PYRIDIN-3-YL)OXY)BENZONITRILE AND PROCESSES OF PREPARATION

(71) Applicant: Dow AgroSciences LLC, Indianapolis, IN (US)

(72) Inventors: Nicholas R. Babij, Indianapolis, IN (US); Qiang Yang, Zionsville, IN (US); Sarah Ryan, Indianapolis, IN (US); Yan Hao, Zionsville, IN (US); Gary Roth, Midland, MI (US); Kaitlyn Gray, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 16/462,199

(22) PCT Filed: Nov. 17, 2017

(86) PCT No.: PCT/US2017/062149
§ 371 (c)(1),
(2) Date: May 17, 2019

(87) PCT Pub. No.: WO2018/094138
PCT Pub. Date: May 24, 2018

(65) Prior Publication Data
US 2019/0276431 A1    Sep. 12, 2019

Related U.S. Application Data

(60) Provisional application No. 62/423,854, filed on Nov. 18, 2016.

(51) Int. Cl.
*C07D 401/06* (2006.01)
*A61K 31/4439* (2006.01)

(52) U.S. Cl.
CPC ........ *C07D 401/06* (2013.01); *A61K 31/4439* (2013.01)

(58) Field of Classification Search
CPC .................................................... C07D 401/06
USPC ....................................................... 546/272.4
See application file for complete search history.

(56) References Cited

U.S. PATENT DOCUMENTS

| | | |
|---|---|---|
| 2012/0088664 A1 | 4/2012 | Renner et al. |
| 2013/0005985 A1 | 1/2013 | Dochnahl et al. |
| 2016/0102072 A1 | 4/2016 | Hoekstra et al. |

FOREIGN PATENT DOCUMENTS

| | | | |
|---|---|---|---|
| WO | 2012177635 A1 | 12/2012 | |
| WO | 2015143188 A1 | 9/2015 | |
| WO | 2016187201 A2 | 11/2016 | |
| WO | WO-2016187201 A2 * | 11/2016 | ........... A01N 43/653 |

OTHER PUBLICATIONS

International Search Report for PCT/US2017/062149, ISA/KR, dated Mar. 14, 2018, all pages.
Written Opinion for PCT/US2017/062149, ISA/KR, dated Mar. 14, 2018, all pages.

* cited by examiner

*Primary Examiner* — Patricia L Morris

(57) ABSTRACT

Provided herein is a process for the preparation of 4-((6-(2-(2,4-difluorophenyl)-1,1-difluoro-2-hydroxy-3-(5-mercapto-1H-1,2,4-triazol-1-yl)propyl)pyridin-3-yl)oxy)benzonitrile.

6 Claims, No Drawings

4-((6-(2-(2,4-DIFLUOROPHENYL)-1,1-DIFLUORO-2-HYDROXY-3-(5-MERCAPTO-1H-1,2,4-TRIAZOL-1-YL)PROPYL)PYRIDIN-3-YL)OXY)BENZONITRILE AND PROCESSES OF PREPARATION

CROSS-REFERENCE TO RELATED APPLICATIONS

The present application is a U.S. National Phase Patent Application based on International Application No. PCT/US2017/062149 filed Nov. 17, 2017, which claims the benefit of U.S. provisional patent application, U.S. Ser. No. 62/423,854, filed Nov. 18, 2016, the entire contents of which are incorporated herein by reference.

FIELD

Provided herein is 4-((6-(2-(2,4-difluorophenyl)-1,1-difluoro-2-hydroxy-3-(5-mercapto-1H-1,2,4-triazol-1-yl)propyl)pyridin-3-yl)oxy)benzonitrile and processes of preparation.

BACKGROUND

U.S. Patent Application Ser. No. 62/163,106 describes inter alia certain metalloenzyme inhibitor compounds and their use as fungicides. The disclosure of this application is expressly incorporated by reference herein. This patent application describes various routes to generate metalloenzyme inhibiting fungicides. It may be advantageous to provide more direct and efficient methods for the preparation of metalloenzyme inhibiting fungicides and related compounds, e.g., by the use of reagents and/or chemical intermediates which provide improved time and cost efficiency.

SUMMARY OF THE DISCLOSURE

Provided herein is the compound 4-((6-(2-(2,4-difluorophenyl)-1,1-difluoro-2-hydroxy-3-(5-mercapto-1H-1,2,4-triazol-1-yl)propyl)pyridin-3-yl)oxy)benzonitrile (I) and processes for its preparation. In one embodiment, provided herein, is a process for the preparation of the compound of the Formula I:

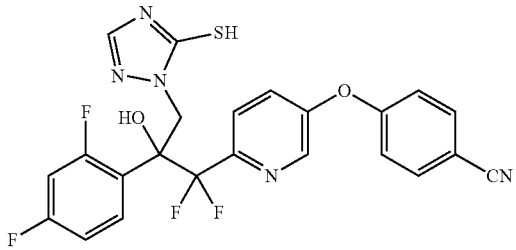

I which comprises contacting a compound of Formula II with a base, elemental sulfur and an acid.

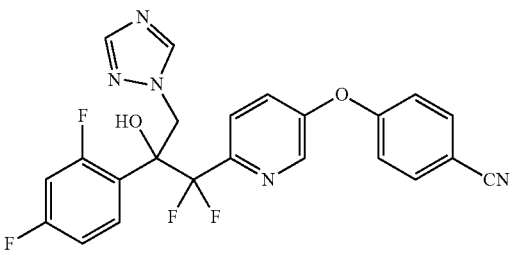

II

The term "halogen" or "halo" refers to one or more halogen atoms, defined as F, Cl, Br, and I.

The term "organometallic" refers to an organic compound containing a metal, especially a compound in which a metal atom is bonded directly to a carbon atom.

Room temperature (RT) is defined herein as about 20° C. to about 25° C.

Throughout the disclosure, references to the compounds of Formula I-II are read as also including optical isomers and salts. Specifically, when compounds of Formula I-II contain a chiral carbon, it is understood that such compounds include optical isomers and racemates thereof. Exemplary salts may include: hydrochloride, hydrobromide, hydroiodide, and the like.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule. For example, the chemical structures of Formulas I and Ia are tautomeric forms of the same molecule.

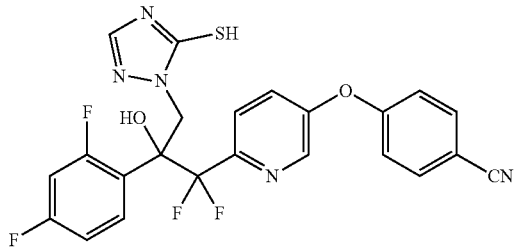

I

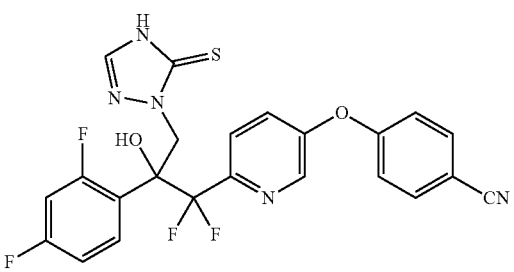

Ia

The embodiments described above are intended merely to be exemplary, and those skilled in the art will recognize, or will be able to ascertain using no more than routine experimentation, numerous equivalents of specific processes, materials and procedures. All such equivalents are considered to be within the scope of the invention and are encompassed by the appended claims.

DETAILED DESCRIPTION 4-((6-(2-(2,4-Difluorophenyl)-1,1-difluoro-2-hydroxy-3-(5-mercapto-1H-1,2,4-triazol-1-yl)propyl)pyridin-3-yl)oxy)benzonitrile (I) is provided herein and may be prepared from 4-((6-(2-(2,4-difluorophenyl)-1,1-difluoro-2-hydroxy-3-(1H-1,2,4-triazol-1-yl)propyl)pyridin-3-yl)oxy)benzonitrile (II) as shown in Example 1.

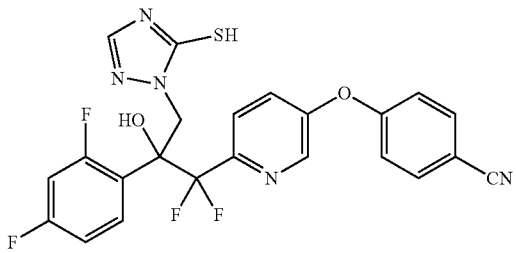

Example 1: Preparation of 4-((6-(2-(2,4-difluorophenyl)-1,1-difluoro-2-hydroxy-3-(5-mercapto-1H-1,2,4-triazol-1-yl)propyl)pyridin-3-yl)oxy)benzonitrile (I)

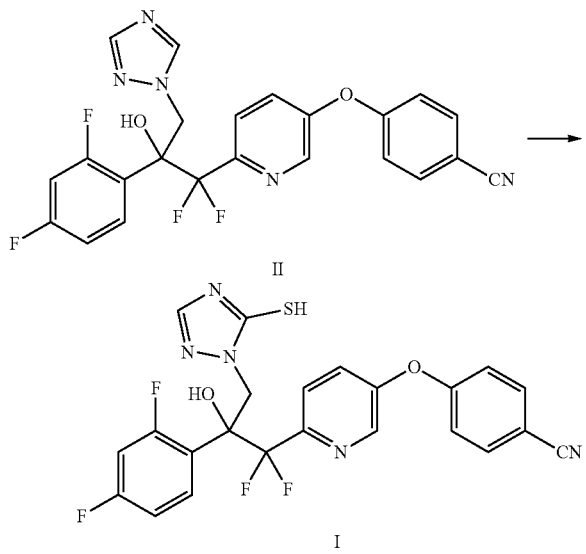

Method A: Use of lithium bis(trimethylsilyl)amide (LiHMDS) in THF.

A 1-L three-neck flask equipped with a temperature probe, a nitrogen inlet and a mechanical stirrer was charged with 4-((6-(2-(2,4-difluorophenyl)-1,1-difluoro-2-hydroxy-3-(1H-1,2,4-triazol-1-yl)propyl)pyridin-3-yl)oxy)benzonitrile (II) (20 g, 42.6 mmol), sulfur (13.66 g, 426 mmol), and THF (85 mL). The reaction mixture was stirred at 323 rpm and cooled to −40° C. Lithium bis(trimethylsilyl)amide (1.5 M solution in THF, 128 mL, 192 mmol) was added via syringe and stirred at 30° C. for 90 min. The reaction was quenched with 4 N HCl and the resulting mixture was stirred for 1 h. The organic layer was washed with brine (2×60 mL), and then saturated aqueous sodium bicarbonate (50 mL). The organic layer was filtered and treated with saturated aqueous sodium thiosulfate (200 mL). The resulting mixture was stirred for 1 h and filtered through filter paper. The organic phase was dried over anhydrous sodium sulfate, filtered, and concentrated to give 21.6 g of a light yellow foam. Acetonitrile (50 mL) was added and the resulting solution was seeded (0.1 g of I) and stirred for 18 h. The suspension was filtered to afford 4.2 g of the title compound. The filtrate was concentrated in vacuo to give a light yellow foam. MTBE was added and stirred at 50° C. for 30 min. The mixture was cooled to 20° C. and the suspension was filtered to afford 11.2 g of the title compound. The MTBE filtrate was concentrated and purified via silica gel column chromatography eluting with an ethyl acetate/hexane gradient to afford 2.8 of the title compound as a white foam. The three lots were combined to afford 18.2 g (85% yield) of the title compound (I). $^1$H NMR (400 MHz, DMSO-$d_6$) δ 13.59 (s, 1H), 8.47 (d, J=2.7 Hz, 1H), 8.18 (s, 1H), 8.00-7.85 (m, 2H), 7.71 (dd, J=8.7, 2.8 Hz, 1H), 7.64 (d, J=8.7 Hz, 1H), 7.38 (td, J=9.0, 6.8 Hz, 1H), 7.27-7.19 (m, 2H), 7.16 (ddd, J=12.0, 9.1, 2.6 Hz, 1H), 6.96 (td, J=8.5, 2.6 Hz, 1H), 6.42 (s, 1H), 5.26-4.82 (m, 2H); $^{19}$F NMR (376 MHz, DMSO-$d_6$) δ 102.20 (td, J=24.5, 8.9 Hz), 108.18 (dd, J=24.8, 17.9 Hz), 111.23 (d, J=8.9 Hz); ESIMS: m/z 502.0 ([M+H]$^+$).

Method B1: Use of lithium bis(trimethylsilyl)amide (LiHMDS) in THF/Toluene.

A 500 mL three-neck flask was fitted with a thermocouple, a condenser with a nitrogen inlet, a septum, and a mechanical stirrer. After flushing with nitrogen, 4-((6-(2-(2,4-difluorophenyl)-1,1-difluoro-2-hydroxy-3-(1H-1,2,4-triazol-1-yl)propyl)pyridin-3-yl)oxy)benzonitrile (II) (7.5 g, 16.0 mmol) was added, followed by dry toluene (100 mL). Sulfur powder (2.3 g, 71.9 mmol) was added. The solution was cooled to 18 to 16° C. and lithium bis(trimethylsilyl)amide (45 mL, 1.0 M solution in THF) was added in portions over 30 min while keeping the temperature of the reaction between 22 to 15° C. After 2.5 h, additional lithium bis(trimethylsilyl)amide (5 mL, 1.0M solution in THF) was added and the mixture was stirred for 1 h. Water (100 mL) was added to the reaction mixture keeping the temperature below 16° C. The mixture was slowly warmed to RT with stirring. The mixture was poured into a separatory funnel and layers were separated. The aqueous phase was treated with 2 N HCl (25 mL) to pH 3. The aqueous layer was extracted with ethyl acetate (2×60 mL). The organic phase was filtered and returned to the separatory funnel, and residual water was separated. The organic phase was concentrated to afford a yellow glass. Toluene (150 mL) was added and some of the toluene was removed on the rotovap. The mixture was filtered and concentrated to about 25 mL. The warm solution was seeded and stirred at RT for about 1 h. The suspension was cooled to 5° C. and stirred for 1 h. The solid was collected via filtration and washed with toluene. The solid was dried to a constant mass to give the title compound as a yellow solid (6.8 g, 80% yield, 94% purity). Analytical data matched the data obtained by using Method A.

Method B2: Use of lithium bis(trimethylsilyl)amide (LiHMDS) in THF/Toluene.

To a 250 mL jacketed reactor was added 4-((6-(2-(2,4-difluorophenyl)-1,1-difluoro-2-hydroxy-3-(1H-1,2,4-triazol-1-yl)propyl)pyridin-3-yl)oxy)benzonitrile (II) (7.5 g, 15.98 mmol), sulfur (5.12 g, 160 mmol), and THF (32 mL) and the mixture was cooled to 30° C. Lithium bis(trimethylsilyl)amide (LiHMDS, 1.0 M solution in toluene, 80 mL, 80 mmol) was added via syringe pump over 45 min. The reaction was stirred at −30° C. for 30 min then quenched with 112 mL of water and the jacket warmed to 20° C. After stirring for 1 h, the layers were separated and the organic layer discarded. The aqueous layer was washed with dichloromethane (75 mL). The aqueous layer was extracted with ethyl acetate (150 mL) and the aqueous layer was discarded. The organic layer was washed with brine (100 mL). Water (75 mL) was added to the organic layer and the pH was adjusted to 5-6 using 2 N HCl. The aqueous layer was discarded. The organic layer was quantified (143.16 g, 5.7 wt %, 8.16 g, 102% in pot yield). The organic layer was atmospherically distilled to about a volume of 85 mL and was heated to 70° C. The mixture was seeded with product crystals and held at 70° C. for 30 min before adding heptane (75 mL) over 10 min. The light slurry was cooled to 20° C. over 10 h. The solids were isolated by filtration and air dried to constant mass giving 4-((6-(2-(2,4-difluorophenyl)-1,1-difluoro-2-hydroxy-3-(5-thioxo-4,5-dihydro-1H-1,2,4-triazol-1-yl)propyl)pyridin-3-yl)oxy)benzonitrile (I) as a white solid (6.35 g, 12.41 mmol, 78% yield). mp 219-222° C.; $^1$H NMR (400 MHz, DMSO-$d_6$) δ 13.59 (s, 1H), 8.47 (d, J=2.7 Hz, 1H), 8.18 (s, 1H), 8.00-7.85 (m, 2H), 7.71 (dd, J=8.7, 2.8 Hz, 1H), 7.64 (d, J=8.7 Hz, 1H), 7.38 (td, J=9.0, 6.8 Hz, 1H), 7.27-7.19 (m, 2H), 7.16 (ddd, J=12.0, 9.1, 2.6 Hz, 1H), 6.96 (td, J=8.5, 2.6 Hz, 1H), 6.42 (s, 1H), 5.26-4.82 (m, 2H); $^{19}$F NMR (376 MHz, DMSO-$d_6$) δ −101.37–104.79 (m), −108.07 (dd, J=23.1, 12.9 Hz), −110.76 (d, J=9.0 Hz); ESIMS: m/z 502.0 ([M+H]$^+$).

Method B3: Use of lithium bis(trimethylsilyl)amide (LiHMDS) in THF/Toluene.

To a jacketed 1-L reactor was charged 4-((6-(2-(2,4-difluorophenyl)-1,1-difluoro-2-hydroxy-3-(1H-1,2,4-triazol-1-yl)propyl)pyridin-3-yl)oxy)benzonitrile (II) (27.96 g, 0.057 mol), followed by sulfur flakes (14.57 g, 0.45 mol). Tetrahydrofuran (THF, 76 g) was added and the mixture was cooled to 2.5° C. To the mixture was added 1.0 M bis(trimethylsilyl)amide solution in toluene (201.1 g, 0.23 mol) over 2.5 h. Upon completing base addition, the reaction mixture was allowed to warm up to 15° C. After 30 minutes, water (343 g) was added slowly over 20 minutes. The organic layer was discarded and the aqueous layer was extracted with ethyl acetate (252 g). The organic layer was washed with 10 wt % NaCl solution (140 g) followed by 10 wt % aqueous acetic acid solution (140 g). The ethyl acetate was removed by distillation replacing the solvent with 2-propanol (319 g) for crystallization. After cooling the reaction mixture to 58° C., the mixture was seeded with product crystals and stirred at 58° C. for 1 h. To the resulting mixture was added water (210 g) at 58° C. over 1 h. The suspension was stirred at 58° C. for 10 h and cooled to 20° C. over 3 h. The crystallized product was isolated by filtration, washed with water (30 g), and air dried to constant mass giving 4-((6-(2-(2,4-difluorophenyl)-1,1-difluoro-2-hydroxy-3-(5-mercapto-1H-1,2,4-triazol-1-yl)propyl)pyridin-3-yl)oxy)benzonitrile (25.52 g, 47.9 mmol, 84% yield). Analytical data matched the data obtained by using Method A.

Method C: Use of Lithium Diisopropylamide (LDA) in THF/Hexanes.

A 100 mL reaction vessel equipped with a temperature probe, a nitrogen inlet, and a mechanical stirrer was charged with 4-((6-(2-(2,4-difluorophenyl)-1,1-difluoro-2-hydroxy-3-(1H-1,2,4-triazol-1-yl)propyl)pyridin-3-yl)oxy)benzonitrile (II) (1 g, 2.13 mmol), sulfur (301 mg, 9.37 mmol), naphthalene as an internal standard (273 mg, 1 equiv), and THF (16 mL) and the reaction flask was cooled to 20° C. A separate 25 mL flask equipped with a magnetic stirring bar and a nitrogen inlet was backfilled with nitrogen and charged with diisopropylamine (1.314 mL, 9.37 mmol) and THF (5.33 mL). The flask was cooled to 0° C. and n-butyllithium (2.5 M in hexanes, 3.75 mL, 9.37 mmol) was added to give a clear, light-yellow homogeneous solution of LDA. The solution of LDA was stirred for 30 min at 0° C. and then was added in increments to the reaction vessel containing II via syringe until the starting material had been nearly all consumed (<4% remaining) as judged by HPLC analysis (overall, 2.75 equivalents of LDA were added). The reaction was quenched with water (15 mL) and diluted with ethyl acetate. The layers were separated and the aqueous layer was determined to have a pH of 11. The aqueous layer was lowered to pH 8 with saturated aqueous ammonium chloride and then extracted with ethyl acetate. The layers were separated. The aqueous layer was lowered to pH 1 with 2 N HCl and then extracted with ethyl acetate. The combined organic layers were dried with anhydrous sodium sulfate, filtered, and concentrated. The crude reaction mixture was dissolved in DCM (residual sulfur was not soluble) and purified via silica gel column chromatography eluting with an ethyl acetate/hexane gradient to afford the title compound (I) as a yellow foam (640 mg, 57%). Analytical data collected from the yellow foam matched the data obtained from the product prepared by using Method A.

Suitable solvents for use in this process step may include THF (tetrahydrofuran), DME (1,2-dimethoxyethane), ether (diethyl ether), MTBE (methyl t-butyl ether), 2-Me-THF (2-methyltetrahydrofuran), toluene, hexanes or dioxane, and mixtures thereof.

Suitable bases for use in this process step may include lithium bis(trimethylsilyl)amide (LiHMDS), sodium bis(trimethylsilyl)amide (NaHMDS), potassium bis(trimethylsilyl)amide (KHMDS), lithium diisopropylamide (LDA), lithium tetramethylpiperidide (LTMP), metal t-butoxides such as lithium t-butoxide, sodium t-butoxide, potassium t-butoxide, metal carbonates, such as lithium carbonate, sodium carbonate, potassium carbonate, cesium carbonate, and mixtures thereof.

Suitable acids for use in this process step may include, but are not limited to, HCl, HBr, $H_2SO_4$, $H_3PO_4$, $HNO_3$, acetic acid, trifluoroacetic acid, and mixtures thereof.

This process step may be conducted at temperatures from about 150° C. to about 80° C., or from about 100° C. to about 40° C.

What is claimed is:

1. A method of making a compound of Formula I

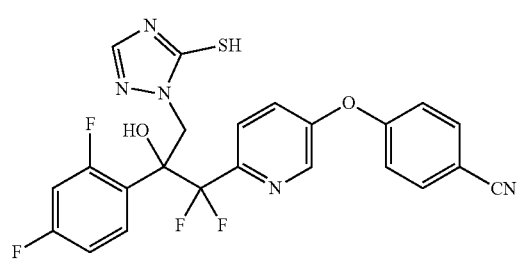

comprising the step of contacting a compound of Formula II

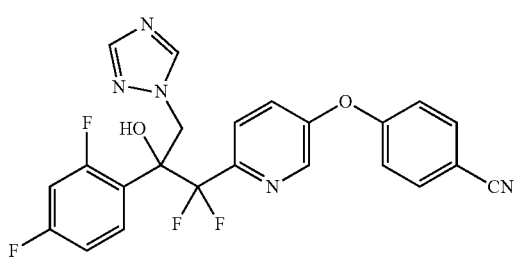

with a base, elemental sulfur, and an acid;
wherein the contacting is carried out between 100° C. and −40° C.

2. The method of claim 1, wherein the base is selected from the group consisting of: LiHMDS, NaHMDS, KHMDS, LDA, LTMP, and mixtures thereof.

3. The method of claim 1, wherein the base is selected from the group consisting of: lithium t-butoxide, sodium t-butoxide, potassium t-butoxide, and mixtures thereof.

4. The method of claim 1, wherein the base is selected from the group consisting of: lithium carbonate, sodium carbonate, potassium carbonate, cesium carbonate, and mixtures thereof.

5. The method of claim 2, further comprising a solvent selected from the group consisting of: THF, DME, ether, MTBE, 2-Me-THF, hexanes, dioxane, toluene, and mixtures thereof.

6. The method of claim 1 wherein the acid is selected from the group consisting of: HCl, HBr, $H_2SO_4$, $H_3PO_4$, $HNO_3$, acetic acid, trifluoroacetic acid, and mixtures thereof.

* * * * *